US012611400B2

(12) United States Patent
Van et al.

(10) Patent No.: US 12,611,400 B2
(45) Date of Patent: Apr. 28, 2026

(54) SOLID LIPID NANO-COMPOSITION CONTAINING BERBERINE AND CINNAMONALDEHYDE EFFECTIVE IN TREATING DIABETES, DYSLIPIDEMIA, AND METHOD OF PREPARING THE SAME

(71) Applicant: Nguyen Anh Van, Hanoi City (VN)

(72) Inventors: Nguyen Anh Van, Hanoi City (VN); Nguyen Duc Nghia, Hanoi City (VN); Kieu Dinh Hung, Hanoi City (VN); Nguyen Thi Ngoc Binh, Hanoi City (VN)

(73) Assignee: Nguyen Anh Van, Hanoi City (VN)

( * ) Notice: Subject to any disclaimer, the term of this patent is extended or adjusted under 35 U.S.C. 154(b) by 670 days.

(21) Appl. No.: 17/925,382

(22) PCT Filed: Dec. 4, 2020

(86) PCT No.: PCT/VN2020/000018
§ 371 (c)(1),
(2) Date: Nov. 15, 2022

(87) PCT Pub. No.: WO2021/232071
PCT Pub. Date: Nov. 18, 2021

(65) Prior Publication Data
US 2023/0181547 A1     Jun. 15, 2023

(30) Foreign Application Priority Data
May 15, 2020    (VN) .............................. 1-2020-02788

(51) Int. Cl.
| | |
|---|---|
| *A01N 43/00* | (2006.01) |
| *A01N 43/46* | (2006.01) |
| *A61K 31/11* | (2006.01) |
| *A61K 31/4375* | (2006.01) |
| *A61K 31/55* | (2006.01) |
| *A61K 47/14* | (2017.01) |
| *A61K 47/24* | (2006.01) |
| *A61K 47/26* | (2006.01) |
| *A61K 47/44* | (2017.01) |
| *A61P 3/06* | (2006.01) |

(52) U.S. Cl.
CPC .......... *A61K 31/4375* (2013.01); *A61K 31/11* (2013.01); *A61K 47/14* (2013.01); *A61K 47/24* (2013.01); *A61K 47/26* (2013.01); *A61K 47/44* (2013.01); *A61P 3/06* (2018.01)

(58) Field of Classification Search
None
See application file for complete search history.

(56) References Cited

FOREIGN PATENT DOCUMENTS

| | | | | | |
|---|---|---|---|---|---|
| CN | 1814149 | A | * | 8/2006 | |
| CN | 102949375 | B | | 4/2015 | |
| CN | 105708799 | A | * | 6/2016 | .......... A61K 31/192 |
| WO | 2015143444 | A1 | | 9/2015 | |
| WO | 2016015634 | A1 | | 2/2016 | |
| WO | 2016161921 | A1 | | 10/2016 | |

OTHER PUBLICATIONS

Zhang, Wei; Xu, Yan-cheng; Guo, Fang-jian; Meng, Ye; Li, Ming-li. Anti-diabetic effects of cinnamaldehyde and berberine and their impacts on retinol-binding protein 4 expression in rats with type 2 diabetes mellitus. Chinese Medical Journal 121(21):p. 2124-2128, Nov. 2008.*

* cited by examiner

*Primary Examiner* — Layla Soroush
(74) *Attorney, Agent, or Firm* — NKL LW; Jae Youn Kim

(57) ABSTRACT

The present invention relates to a composition effective in treating diabetes and dyslipidemia prepared according to the solid lipid nanotechnology from two natural phytochemical active ingredients: cinnamaldehyde extracted from the Vietnamese cinnamon and berberine as a bioactive compound extracted from several plants, including a group of shrubs called *Berberis*. Via testing, all of the composition of the present invention has shown to have low toxicity and great bioavailability, reduced insulin resistance that allows the sugar level in blood to more effectively induce reduction of insulin, hyperglycolysis that aids the body in cellular sugar decomposition, reduced sugar production in the liver, carbohydrate decomposition slowed down in the intestines, and an increasing in the number of beneficial microbes in the intestines. The composition is effective in reducing the total cholesterol level (TC), and non-HDL-cholesterol, and has a tendency to reduce TG level.

1 Claim, 2 Drawing Sheets

(a) Cinnamaldehyde            (b) Cinnamic acid            (c) Cinnamyl acetate (a) α-Thujene            (b)        α-            (c) α-Cubebene
                         Terpineol

SOLID LIPID NANO-COMPOSITION CONTAINING BERBERINE AND CINNAMONALDEHYDE EFFECTIVE IN TREATING DIABETES, DYSLIPIDEMIA, AND METHOD OF PREPARING THE SAME

FIELD OF THE INVENTION

The present invention relates to a solid lipid nano-composition containing berberine and cinnamonaldehyde effective in treating diabetes and dyslipidemia, and a method of preparing the same.

BACKGROUND OF THE INVENTION

Berberine and Its Pharmacological Effects

Berberine is an alkaloid isoquinoline, the main ingredient that can be extracted from several herbs, including a group of shrubs called *Berberis*. The chemical structure of berberine is shown in FIG. 1 (see the Drawing used in the present invention).

The herbs containing berberine have been used to treat intestinal infection, particularly bacterial diarrhea. Berberine has been tested in hundreds of different studies. It has a great impact on various biological systems. After oral administration, Berberine is introduced into the body and delivered into the blood, then into the body cells. Within the cells, it binds with different "molecular targets" and changes their functions. This is similar to how pharmaceutical drugs function. One of the main functions of berberine is to activate an enzyme within the cells called AMP-activated protein kinase (AMPK). AMPK is found in the cells of different organs, including brain, muscles, kidneys, heart, and liver. This enzyme plays the main role in metabolic regulation. Berberine also affects other molecules in the cells and can even affect the on/off genes. Berberine has an impact on the body at a molecular level and has many functions within the cells.

Cinnamon

Cinnamon (*Cinnamomum zeylanicum*, and *Cinnamomum cassia*), is a tree of the Lauraceae family in tropical medicine that dates back to ancient times. Cinnamon is one of the most important spices that are widely used all over the world. Cinnamon mainly contains important oils and other derivatives, such as cinnamonaldehyde, cinnamic acid, and cinnamate. Other than making an antioxidative, anti-inflammatory, anticoagulant, antibiotic, anticarcinogenic, lipid lowering, and blood pressure reducing drug, cinnamon has also been reported to have activities against neurological disorders, such as Parkinson's disease and Alzheimer's disease. This evaluation illustrates the potential pharmacology of cinnamon and its daily uses.

SUMMARY OF THE INVENTION

The objective of the present invention is to provide a composition of low toxicity and great bioavailability, and enhance the ability to reduce insulin resistance, allowing the sugar level in blood to more effectively induce the reduction of insulin hormone. Hyperglycolysis allows the body to decompose sugar in cells. Sugar production is reduced in the liver. Carbohydrate decomposition is slowed down in the intestines. The number of beneficial microbes increases in the intestines.

To achieve the above objective, the composition is prepared from a bicomponent system, according to the solid lipid nanotechnology, comprising cinnamonaldehyde extracted from the Vietnamese cinnamon and berberine as a bioactive compound extracted from several plants, including a group of shrubs called *Berberis*.

The composition comprises the following components:
(a) Solid lipid nano berberine: 5-25%;
(b) Solid lipid nano cinnamonaldehyde: 1-15%;
(c) Glycerol monostearate: 5-15%;
(d) Soy bean oil: 60-80%;
(e) Lecithin: 5-10%;
(f) Tween 80: 0.01-1%.

The present invention provides a process for preparing the aforementioned composition, comprising the following steps:
i) Producing a solution of solid lipid nano berberine;
ii) Producing a bicomponent system of solid lipid nano berberine/cinnamonaldehyde;
iii) Producing a pre-composition; and
iv) Obtaining a finished composition.

DETAILED DESCRIPTION OF THE INVENTION

Figures 1, 2:
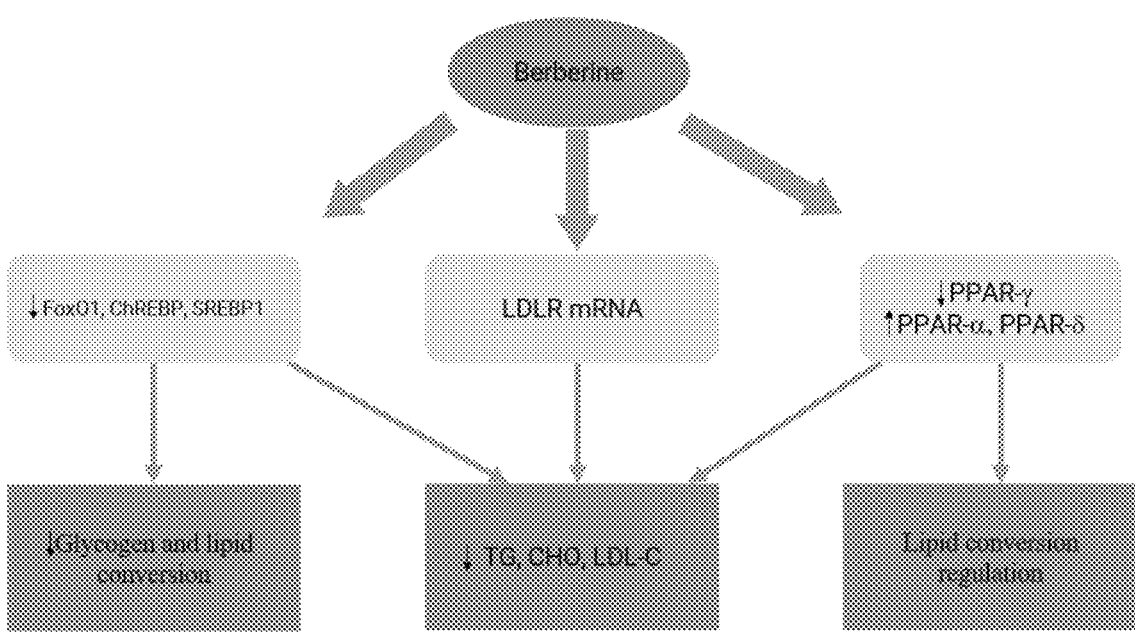
FIG. 1 shows the chemical structure of berberine.
FIG. 2 shows the main mechanisms of berberine in lipid conversion.
Figures 3, 4, 5:
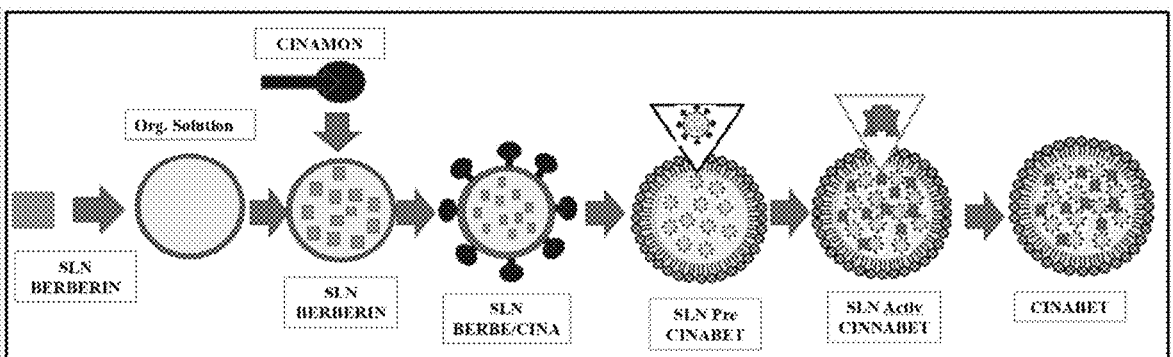
FIG. 3, and FIG. 4 show the chemical structures of some important components present in cinnamon.
FIG. 5 illustrates a process for preparing a composition that is effective in treating diabetes and dyslipidemia.

The composition according to the invention comprises the following components:
(a) Solid lipid nano berberine: 5-25%;
(b) Solid lipid nano cinnamonaldehyde: 1-15%;
(c) Glycerol monostearate: 5-15%;
(d) Soy bean oil: 60-80%;
(e) Lecithin: 5-10%;
(f) Tween 80: 0.01-1%.

The process for preparing the composition according to the invention undergoes the following steps:
Cinnamonaldehyde is extracted from Cinnamon from Quang Nam, Vietnam by steam distillation, with the achieved cinnamonaldehyde content is over 98%.
Berberine hydrochloride is purchased from Northeast Pharmaceutical Group Co. LTD. (China).
Berberine/cinnamonaldehyde solid lipid nanoparticles are purchased from Vietlife Nano Biological Manufactory) with the following parameters: the average nanoparticle size of 15.8 nm. The berberine content in the nanoparticles is over 22%, and the cinnamonaldehyde content of 12%.
In addition, there are included excipient materials such as glyceril monostearate, stearic acid, magnesium stearate, Tween 80, lecithin, Gac oil, and soybean oil. All of these are raw materials that meet the basic standards for use as pharmaceutical formulative materials in accordance with the regulations.
Equipments used in the invention include a heated gelating device, a temperature adjuster, vacuum forming device, control mixer.
Step 1: Producing a Solution of Solid Lipid Nano Berberine:
Add solid lipid nano berberine to a reaction flask 1 containing 96% ethyl alcohol under heating at 40-50° C. until the solid lipid nano berberine particles are completely dissolved. Boil and stir the mixture at 70-80° C. Obtain solid lipid nano berberine in the ethyl alcohol solvent. Transfer the mixture from the reaction flask 1 to a reaction flask 2.

Step 2: Producing a Bicomponent System of Solid Lipid Nano Berberine/Cinnamonaldehyde:

Next, add cinnamonaldehyde to the above solid lipid nano berberine solution. Boil and evenly stir the solution at 60-80° C., preferably 70° C. After about 50-70 minutes, preferably 60 minutes, raise the temperature to 90-120° C., preferably 100° C., to remove the ethyl alcohol solvent. Boil and evenly stir the mixture at this temperature in about 100-130 minutes, preferably 120 minutes, to produce a bicomponent system of solid lipid nano berberine/cinnamonaldehyde.

Step 3: Producing a Pre-Composition:

Add soy bean oil, lecithin, and Tween 80 to the reaction flask; heat the mixture at 90-100° C.; evenly stir the reaction mixture at high speed until the formation of a transparent gel; stop the reaction; obtain a pre-composition.

Step 4: Obtaining a Finished Composition:

Adjust the contents of the organic sol-gel components to achieve the standard technical parameters, which include the content of solid lipid nano berberine and the content of solid lipid nano cinnamonaldehyde. The formation of smart gel at gel resolution temperature comprises gelation at normal temperature (room temperature) or storage temperature (below 24° C.).

EXAMPLES

Example 1: Method of Preparing a Composition; the Example is Used to Disclose the Present Invention, Not to Limit the Scope of the Present Invention The preparation of one soft capsule containing 500 mg of the composition requires the following components:

(a) Solid lipid nano berberine: 10 mg;
(b) Solid lipid nano cinnamonaldehyde: 5 mg;
(c) Glycerol monostearate: 50 mg;
(d) Soy bean oil: 400 mg;
(e) Lecithin: 30 mg;
(f) Tween 80: 5 mg.

10 mg of solid lipid nano berberine was added to a reaction flask 1 already containing 96% ethyl alcohol under heating at 50° C. until the solid lipid nano berberine particles were completely dissolved, raised to 80° C. while stirring to obtain solid lipid nano berberine in ethyl alcohol. Then the mixture was transferred to a reaction flask 2. Next, 5 mg of cinnamonaldehyde was added to the solution, heated and evenly stirred at 70° C. After about 60 minutes, the temperature was raised to 100° C. to remove the ethyl alcohol solvent. After boiling and even stirring at this temperature for about 120 minutes, a bicomponent system of solid lipid nano berberine/cinnamonaldehyde was obtained. To the reaction flask was added 400 mg of soy bean oil, 30 mg of lecithin, and 5 mg of tween 80, maintained at 100° C. under high-speed stirring until a transparent gel was obtained. Then the reaction was stopped. The contents of the organic sol-gel components were adjusted to achieve the standard technical parameters, including the content of solid lipid nano berberine and the content of solid lipid nano cinnamonaldehyde. The formation of smart gel at gel resolution temperature comprises gelation at normal temperature (room temperature) or storage temperature (below 24° C.).

Example 2: Evaluation of Dyslipidemia Regulation Effects of the Composition in Empirical Endogenous Models The test on white mice was divided into 5 batches, each batch having 10 animals. The batches were subjected to injection and oral administration as follows:

Batch 1 (biological control): 0.9% saline was intraperitoneally injected at a volume of 0.1 mL/10 g mouse body weight and 0.2 mL/10 g distilled water was orally administered.

Batch 2 (model): 2% P-407 solution was intraperitoneally injected at 200 mg/kg (0.1 mL/10 g), and 0.2 mL/10 g distilled water was orally administered.

Batch 3 (positive control): 2% P-407 solution was intraperitoneally injected at 200 mg/kg (0.1 mL/10 g), and 100 mg/kg (0.2 mL/10 g) atorvastatin was orally administered.

Batch 4: 2% P-407 solution was intraperitoneally injected at 200 mg/kg (0.1 mL/10 g), the composition was orally administered at 0.24 g/kg/day (equivalent to the clinical intended dose), at 0.2 mL/10 g.

Batch 5: 2% P-407 solution was intraperitoneally injected at 200 mg/kg dose (0.1 mL/10 g), the composition was orally administered at dosage 0.72 g/kg/day (3 times as much as the clinical intended dose), at 0.2 mL/10 g.

White mice were subjected to oral administration of distilled water and the sample drug in 7 continuous days before the intraperitoneal injection with P-407 solution. After P-407 injection, the mice were left to starve completely but were free to drink water. After 24 hours from the P-407 injection, all of the mice received carotid arterial blood sampling for TG, TC, and HDL-C quantitative testing. Non-HDL-C levels were calculated based on the following formula:

$$\text{Non-HDL-C} = \text{TC} - \text{HDL-C} \ (\text{mmol/L})$$

Test Results
Total Cholesterol Levels

TABLE 1

| Effects of the composition on the total cholesterol level in white mouse blood | | | | |
|---|---|---|---|---|
| Study batch (n = 10) | Total cholesterol level (mmol/L) | Reduction in comparison with the model batch | p-value in comparison with Batch 2 | p-value in comparison with Batch 3 |
| Batch 2: Model | 8.70 ± 1.76 | | | |
| Batch 3: 100 mg/kg Atorvastatin | 8.20 ± 1.01 | 5.7% | p > 0.01 | |
| Batch 4: 0.24 g/kg/day composition | 7.21 ± 0.72 | 17.1% | p < 0.05 | p < 0.05 |
| Batch 5: 0.72 g/kg/day composition | 7.21 ± 1.16 | 17.1% | p < 0.05 | p > 0.05 |

Results from Table 1 showed that the oral 100 mg/kg atorvastatin batch reduced the total cholesterol level in comparison with the model batch (5.7% reduction). However, the difference showed no statistical significance (p>0.05).

The oral composition batches at both doses of 0.24 g/kg/day and 0.72 g/kg/day reduced the total cholesterol level in comparison with the model batch (17.1% reduction), with the difference being statistically significant (p<0.05).

Triglyceride Levels

TABLE 2

| Effects of the composition on triglyceride level in white mouse blood | | | | |
|---|---|---|---|---|
| Study batch (n = 10) | Triglyceride level (mmol/L) | Reduction in comparison with the model batch | p-value in comparison with Batch 2 | p in comparison with Batch 3 |
| Batch 2: Mô hình | 6.68 ± 2.19 | | | |
| Batch 3: 100 mg/kg Atorvastatin | 9.77 ± 1.05 | −46.3% | p < 0.01 | |
| Batch 4: 0.24 g/kg/day composition | 4.34 ± 1.44 | 35.0% | p < 0.05 | p < 0.001 |
| Batch 5: 0.72 g/kg/day composition | 5.81 ± 1.77 | 13.0% | p > 0.05 | p < 0.001 |

Results from Table 2 showed that all oral 100 mg/kg atorvastatin batches did not reduce the triglyceride level in comparison with the model batch, with the difference being statistically significant (p<0.01).

The oral low dose composition batch (0.24 g/kg/day) clearly reduced the triglyceride level in comparison with the model batch (35% reduction), with the difference being statistically significant (p<0.05).

The oral high dose composition batch (0.72 g/kg/day) tended to reduce the triglyceride level in comparison with the model batch. However, the difference showed no statistical significance (p>0.05).

The composition at both doses was effective in reducing triglyceride better than atorvastatin, with the difference being statistically significant (p<0.001).

HDL-Cholesterol Levels

TABLE 3

| Effects of the composition on HDL-cholesterol concentration in white mouse blood | | | |
|---|---|---|---|
| Study batch (n = 10) | HDL-C level (mmol/L) | p in comparison with batch 2 | p in comparison with batch 3 |
| Batch 2: Model | 1.78 ± 0.64 | | |
| Batch 3: 100 mg/kg Atorvastatin | 2.12 ± 0.41 (↑ 19.1%) | p > 0.05 | |
| Batch 4: 0.24 g/kg/day composition | 1.53 ± 0.36 (↓ 14.0%) | p > 0.05 | p < 0.01 |
| Batch 5: 0.72 g/kg/day composition | 1.53 ± 0.42 (↓ 14.0%) | p > 0.05 | p < 0.01 |

Results from Table 3 showed that in the oral 100 mg/kg/day atorvastatin batch, there was a tendency to increase the HDL-C level in comparison with the model batch. However, the difference showed no statistical significance (p>0.05).

The oral composition batches at both doses of 0.24 g/kg/day and 0.72 g/kg/day did not increase the HDL-C level in comparison with the model batch, with the difference being not statistically significant (p>0.05).

Non-HDL-Cholesterol Levels

TABLE 4

| Effects of the composition on non-HDL-cholesterol level in white mouse blood | | | | |
|---|---|---|---|---|
| Study batch (n = 10) | Non-HDL-cholesterol level (mmol/L) | Reduction in comparison with the model | p in comparison with batch 2 | p in comparison with batch 3 |
| Batch 2: Model | 6.92 ± 1.47 | | | |
| Batch 3: 100 mg/kg Atorvastatin | 6.08 ± 0.88 | 12.1% | p > 0.05 | |
| Batch 4: 0.24 g/kg/day composition | 5.68 ± 0.77 | 17.9% | p < 0.05 | p > 0.05 |
| Batch 5: 0.72 g/kg/day composition | 5.68 ± 0.94 | 17.9% | p < 0.05 | p > 0.05 |

Results from Table 4 showed that the oral 100 mg/kg atorvastatin batch tended to reduce the non-HDL cholesterol level in comparison with the model batch, in which the difference showed no statistical significance (p>0.05).

The oral composition batches at both doses reduced the non-HDL cholesterol level, which was statistically significant in comparison with the model batch (17.9% reduction) (p<0.05).

CONCLUSION

The 0.24 g/kg/day composition (equivalent to the clinical intended dose, computed based on the coefficient 12) reduced the total cholesterol (TC), triglyceride (TG), and non-HDL-cholesterol (non-HDL-C) levels in comparison with the model batch. The low dose composition did not increase the HDL-cholesterol level in the white mouse models of P-407-induced dyslipidemia.

The high dose Vietlife composition (0.72 g/kg/day) (3 times as much as the clinical intended dose in human) was effective in reducing the total cholesterol (TC) and non-HDL-cholesterol (non-HDL-C) levels, and tended to reduce the triglyceride (TG) level. The high dose composition did not increase the HDL-cholesterol level in the white mouse models of P-407-induced dyslipidemia.

The invention claimed is:

1. A process for preparing a composition effective in treating type 2 diabetes and dyslipidemia, the composition comprising:
   (a) Solid lipid nanoparticles of berberine: 5-25%;
   (b) Solid lipid nanoparticles of cinnamaldehyde: 1-15%;
   (c) Glycerol monostearate: 5-15%;
   (d) Soybean oil: 60-80%;
   (e) Lecithin: 5-10%; and
   (f) polysorbate 80:0.01-1%, the process the steps comprising:
   i) producing a solution of solid lipid berberine, wherein the solid lipid nanoparticles of berberine are added to 96% ethyl alcohol under heating at 40-50° C. until the solid lipid nanoparticles of berberine are completely dissolved; then the solution is heated and stirred at 70-80° C. to obtain solid lipid nanoparticles of berberine in the ethyl alcohol solvent;
   ii) producing a bicomponent system of solid lipid nanoparticles of berberine and cinnamaldehyde wherein cinnamaldehyde is added to the solution of solid lipid nanoparticles of berberine, followed by heating and evenly stirring at 60-80° C.; after about 50-70 minutes, the temperature is raised to 90-120° C., to remove the ethyl alcohol solvent, followed by boiling and evenly stirring at this temperature for about 100-130 minutes, to form the bicomponent system of solid lipid nanoparticles of berberine and cinnamaldehyde;

iii) producing a pre-composition, wherein a mixture of glycerol monostearate soybean oil, lecithin, and polysorbate 80 are combined and heated at 90-100° C.; the mixture is evenly stirred forming a transparent gel; and iv) obtaining a finished composition, wherein solid lipid nanoparticles of berberine and the solid lipid nanoparticles of cinnamaldehyde are combined with the pre-composition transparent gel of iii) forming the finished composition in gel form at room temperature or storage temperature below 24° C.

\* \* \* \* \*